United States Patent

Baba et al.

[11] Patent Number: 5,849,272
[45] Date of Patent: Dec. 15, 1998

[54] ULTRAVIOLET ABSORBING COMPOSITION

[75] Inventors: Katsuya Baba; Toshihito Yabu; Shoji Nishiyama; Kenzo Ito, all of Yokohama, Japan

[73] Assignee: Shiseido Co., Ltd., Tokyo, Japan

[21] Appl. No.: 806,162

[22] Filed: Feb. 25, 1997

[30] Foreign Application Priority Data

Feb. 26, 1996 [JP] Japan ................................. 8-065400
Feb. 12, 1997 [JP] Japan ................................. 9-044596

[51] Int. Cl.$^6$ .............................................. A61K 1/021
[52] U.S. Cl. ........................... 424/59; 424/401; 514/844; 514/845; 514/846
[58] Field of Search ............. 424/401, 59; 514/844–846

[56] References Cited

U.S. PATENT DOCUMENTS 4,699,779 10/1987 Palinczar .
4,731,242 3/1988 Palinczar .
5,489,431 2/1996 Ascione et al. .

FOREIGN PATENT DOCUMENTS 05117136 of 0000 Japan .
61-215315 9/1986 Japan .
61-215316 9/1986 Japan .
61-215316 A 9/1986 Japan .
61-215317 9/1986 Japan .
61-215318 9/1986 Japan .
61-215319 A 9/1986 Japan .
2 105 190 3/1983 United Kingdom .
WO 94/10971 5/1994 WIPO .

Primary Examiner—Jyothsna Venkat
Attorney, Agent, or Firm—Ronald R. Snider

[57] ABSTRACT

The ultraviolet absorbing composition in accordance with the present invention comprises the following ingredients (A) and (B):

(A) 4-tert-butyl-4'-methoxydibenzoylmethane; and (B) a diester which is liquid at 20° C. and has a structure represented by the following general formula (1):

$$R_1OOC—(CH_2)n—COOR_2 \qquad (1)$$

wherein each of $R_1$ and $R_2$ is an alkyl group, an alkenyl group, a hydroxyalkyl group, or a hydroxyalkenyl group each having 1 to 19 carbon atoms, and n is an integer of 0 to 6. In the present invention, crystals of (A) are prevented from depositing by using a diester of (B) togetherwith and an ultraviolet absorbing composition in which (A) can be stably compounded in a high concentration and which exhibits excellent feel of use and safety can be obtained thereby.

5 Claims, No Drawings

ULTRAVIOLET ABSORBING COMPOSITION

RELATED APPLICATIONS

This application claims the priority of Japanese Patent Application No. 8-65400 filed on Feb. 26, 1996, and Japanese Patent Application which title is ULTRAVIOLET ABSORBING COMPOSITION and which inventors are Katsuya BABA, Toshihito YABU, Shoji NISHIYAMA, and Kenzo ITO filed on Feb. 12, 1997 by SHISEIDO CO., LTD. as applicant, which are incorporated herein by reference.

1. Field of the Invention

The present invention relates to an ultraviolet absorbing composition and, in particular, to improvement in stability over time, feel of use, or the like of a composition in which 4-tert-butyl-4'-methoxydibenzoylmethane, which is a hardly soluble UV-A absorber, is compounded.

2. Background of the Invention

Ultraviolet rays contained in sunbeams are classified into long wavelength ultraviolet rays (UV-A) of 400 nm to 320 nm, medium wavelength ultraviolet rays (UV-B) of 320 nm to 280 nm, and short wavelength ultraviolet rays of less than 280 nm. Among them, ultraviolet rays having a wavelength of 290 nm or less are absorbed by ozone layers and do not reach the surface of the earth.

The ultraviolet rays in UV-A and UV-B regions reaching the surface of the earth exert various influences upon human skin. Of the ultraviolet rays reaching the surface of the earth, UV-B forms erythemas and blisters in the skin, while accelerating melanin formation. On the other hand, UV-A browns the skin, accelerates lowering of elasticity in the skin and wrinkling, enhances these reactions in some kinds of patients, and may cause photo-toxicity or photo-allergy. In order to protect the skin from such toxicity of ultraviolet rays, various kinds of ultraviolet absorbers have been developed.

Among such absorbers, 4-tert-butyl-4'-methoxydibenzoylmethane has been remarked as a substance for absorbing UV- A with a relatively long wavelength. 4-tert-butyl-4'-methoxydibenzoylmethane, however, is solid and hardly soluble in both water and oil so as to have a low compatibility with respect to bases of cosmetics and medical external preparations for skin, whereby crystals of 4-tert-butyl-4'-methoxydibenzoylmethane may deposit over time. Various studies have been made in order to solve these problems. For example, a method in which a liquid polyhydric alcohol fatty acid ester is compounded together with 4-tert-butyl-4'-methoxy dibenzoylmethane is disclosed in Japanese Unexamined Patent Publication No. 61-215315, a method in which an ester of a $C_{9-31}$ acid and a $C_{8-31}$ alcohol is compounded together therewith is disclosed in Japanese Unexamined Patent Publication No. 61-215316, and a method in which an oil having an iodine value of 70 or higher is compounded together therewith is disclosed in Japanese Unexamined Patent Publication No. 61-215317.

The cosmetics or medical external preparations for skin including these oils, however, may have been problematic in that oily feel or stickiness occurs therein. Also, when a large amount of a liquid polyhydric alcohol fatty acid ester is compounded so as to compound a high concentration of 4-tert-butyl-4'-methoxy dibenzoylmethane, there may be cases where irritation such as itch or stingingness occurs.

DISCLOSURE OF THE INVENTION

In view of the foregoing problems of the prior art, it is an object of the present invention to provide a composition in which 4-tert-butyl-4'-methoxy dibenzoylmethane, which is a hardly soluble UV-A absorber, can be stably compounded even in a high concentration in it and which is free from oily feel and sticky feel, yields a refreshing feel of use, exhibits a high safety, and has an excellent protecting effect against ultraviolet rays.

As a result of diligent studies performed by the inventors to achieve the above-mentioned object, it has been found that when a specific diester is used together with 4-tert-butyl-4'-methoxydibenzoylmethane, an ultraviolet absorbing composition in which 4-tert - butyl-4'-methoxydibenzoylmethane can be stably compounded in a high concentration and exhibits excellent feel of use and safety can be obtained. Thus, the present invention has been accomplished.

Namely, the ultraviolet absorbing composition in accordance with the present invention comprises the following ingredients (A) and (B):

(A) 4-tert-butyl-4'-methoxydibenzoylmethane; and (B) a diester which is liquid at 20° C. and has a structure represented by the following general formula (1):

$$R_1OOC-(CH_2)n-COOR_2 \quad (1)$$

wherein each of $R_1$ and $R_2$ is an alkyl group, an alkenyl group, a hydroxyalkyl group, or a hydroxyalkenyl group each having 1 to 19 carbon atoms, and n is an integer of 0 to 6.

EXAMPLES 4-tert-butyl-4'-methoxydibenzoylmethane in the above-mentioned ingredient (A) used in the present invention may be manufactured according to a method disclosed in Japanese Unexamined Patent Publication No. 55-66535, for example. Also, as a commercially available product, Parsol 1789 (manufactured by Givaudan) may be used, for example. 4-tert-butyl-4'-methoxydibenzoylmethane is an excellent UV-A absorber having its maximum absorption at about 330 to 360 nm. Though the compounding amount thereof is appropriately selected according to an expected ultraviolet absorbing effect and, therefore, is not restricted in particular; it is usually compounded in the whole composition by 0.1 to 20 weight %, preferably 0.1 to 10 weight %. An ultraviolet protecting effect may not be obtained enough when the amount is too less, whereas a sufficient effect may be obtained with 20 weight % if the composition is a cosmetic or an external preparation.

The diester of (B), which is the other essential ingredient in the present invention, is a diester of a saturated dicarboxylic acid represented by the above-mentioned general formula (1) and is liquid at 20° C. In general formula (1), $R_1$ and $R_2$ may be identical or different and may be any of alkyl groups, alkenyl groups, hydroxyalkyl groups, or hydroxyalkenyl groups each having 1 to 19 carbon atoms. Preferably, $R_1$ and $R_2$ are identical groups since they can easily be obtained or manufactured. These groups may be any of straight chains, branched chains, and cyclic chains. $R_1$ and $R_2$ are preferably alkyl groups each having 1 to 8 carbon atoms and more preferably alkyl groups each having 4 to 8 carbon atoms.

Also, while n is an integer of 0 to 6, it is preferably an integer of 2 to 4 and more preferably 2 or 4.

In the above-mentioned general formula (1), oily feel or stickiness may unfavorably occur in the composition when the number of carbon atoms in $R_1$ and $R_2$ or the value of n is too large. Also, a diester which is solid or half solid at 20° C. is unfavorable in terms of feel of use and stability over time of the composition.

The diester used in the present invention is a known substance, and a commercially available product may be used therefor. Of course, it can be manufactured by means of a known reaction. For example, it can be manufactured by a known esterification reaction from a saturated dicarboxylic acid represented by a formula of HOOC—(CH$_2$)n—COOH, wherein n is an integer of 0 to 6, or an acid anhydride thereof.

Examples of the diester used in the present invention include dioctyl oxalate, dimethyl malonate, diethyl malonate, dibutyl malonate, di-2-ethylhexyl malonate, diethyl succinate, dihexyl succinate, diisopropyl succinate, dihexyl succinate, dioctyl succinate, diethyl glutarate, dipropyl adipate, diisopropyl adipate, diisobutyl adipate, diethyl suberate, diallyl oxalate, di-2-hydroxyhexyl malonate, and di-(4-hydroxl-1-butenyl)succinate. Either one or more of these may be used as the diester in the present invention.

Of the above-mentioned diesters, dioctyl succinate and diisopropyl adipate are preferable, and dioctyl succinate is particularly preferable. Dioctyl succinate is a colorless and odorless liquid. Though diisopropyl adipate is a colorless liquid, a slight odor may be felt when a large amount thereof is compounded.

Though 4-tert-butyl-4'-methoxydibenzoylmethane of (A) exhibits a high ultraviolet-absorbing effect depending on its compounding amount, due to its low compatibility with respect to bases for cosmetics and external preparations for skin, crystals thereof are more likely to deposit in the composition as a larger amount thereof is compounded.

In accordance with the present invention, as the above-mentioned diester of (B) is compounded in the oil phase of the composition together with (A), an ultraviolet absorbing composition excellent in its feel of use and safety, while overcoming the above-mentioned problems, can be obtained. Such effects of (B) upon (A), which are not described in any of the above-mentioned prior art, have been found by the inventors for the first time.

In the ultraviolet absorbing composition in accordance with the present invention, in order to stably compound 4-tert-butyl-4'-methoxydibenzoylmethane of (A) in the composition, the compounding amount of diester (B) is preferably at least one third of the compounding amount of (A) in the composition in terms of weight. Here, even when compounded in excess in the composition of the present invention, this diester does not inhibit the effects of the present invention. Though not restricted in particular, the compounding amount of the diester in the whole composition in accordance with the present invention is normally within the range of 0.01 to 50 weight %, preferably 0.5 to 20 weight %. Too large amount may cause oily feel of use in the composition.

Also, when the ratio of the oil phase with respect to the composition is less than 100%, for example, as in the case of an emulsion, in order to compound a predetermined amount of (A) in the composition, it is necessary for (A) to have a higher concentration in the oil phase as the ratio of the oil phase is lower. Even in a small amount, the diester used in the present invention can prevent crystals of (A) from depositing. Also, even when a large amount of the diester is compounded in the oil phase, it generates neither stickiness nor irritation. Accordingly, it is very useful when a large amount of (A) is compounded in such an emulsion. For example, even in cases where the concentration of (A) in the oil phase is as high as 5 weight % or more, when diester of (B) is compounded in the oil phase such that its concentration in the oil phase becomes one third or more with respect to (A) in terms of weight %, a composition in which crystals of (A) are prevented from depositing and which exhibits excellent feel of use and safety can be obtained.

As explained in the foregoing, the composition in accordance with the present invention can exhibit high UV-A absorbing effects, while being excellent in feel of use, stability, and safety. Accordingly, it is very useful as a sun-protecting composition applying on skin or hair for protecting them from ultraviolet rays.

The ultraviolet absorbing composition in accordance with the present invention can be manufactured according to a normal method, and it's form is not restricted in particular as long as it can exhibit effects of the present invention. For example, it can be formed as basic cosmetic preparations such as lotion, milky lotion, cream, and oil; makeup cosmetic preparations such as foundation, rouge for lip, cheek rouge, eye shadow, and eyebrow; or cosmetics for hair such as hair-styling preparation, hair-conditioner, hair lotion, and hair liquid. Here, as needed, they can take various forms such as gel, stick, spray, mousse, and roll-on. The ultraviolet absorbing composition of the present invention is also applicable as a medical cosmetic preparation, a medical composition, or the like.

In addition to the above-mentioned essential ingredients, ingredients which are used in cosmetics or medical external preparations for skin normally can be compounded in the composition of the present invention within the qualitative and quantitative ranges by which the object and effects of the present invention are not lost. These includes surfactants, aqueous media, oily ingredients, higher alcohols, natural and synthetic polymers, metal-ion blocking agents, water-soluble and oil-soluble polymers, inorganic and organic pigments, inorganic and organic clay minerals, inorganic and organic pigments treated with metallic soup or silicon, coloring materials such as organic dyes, antiseptics, antioxidants, colorants, thickeners, pH-adjusting agents, perfumes, ultraviolet absorbers, humectants, blood circulation-accelerating agents, chilling agents, antiperspirants, bactericides, and skin-activating agents.

Examples of lipophilic nonionic surfactants include sorbitan fatty acid esters such as sorbitan monooleate, sorbitan monoisostearale, sorbitan monolaurate, sorbitan monopalmitate, sorbitan monostearate, sorbitan sesquioleate, sorbitan trioleate, diglycerol sorbitan penta-2-ethylhexanoate, and diglycerol sorbitan tetra-2-ethylhexanoate; esters of glycerin or polyglycerin and fatty acids such as mono-cottonseed fatty acid glycerin ester, glyceryl monoerucate, glyceryl sesquioleate, glyceryl monostearate, diglyceryl diisostearate, glyceryl $\alpha,\alpha'$-pyroglutamate oleate, and glyceryl malate monostearate; propylene glycol fatty acid esters such as propylene glycol monostearate; hydrogenated castor oil derivatives; and glyceryl alkyl ethers.

Examples of hydrophilic nonionic surfactants include POE sorbitan fatty acid esters such as POE sorbitan monooleate, POE sorbitan monostearate, and POE sorbitan tetraoleate; POE sorbitol fatty acid esters such as POE sorbitol monolaurate, POE sorbitol monooleate, POE sorbitol pentaoleate, and POE sorbitol monostearate; POE fatty acid esters such as POE monooleate, POE distearate, and ethylene glycol distearate; POE alkyl ethers such as POE lauryl ether, POE oleyl ether, POE stearyl ether, POE behenyl ether, POE 2-octyldodecyl ether, and POE cholestanol ether; POE alkylphenyl ethers such as POE octylphenyl ether, POE nonylphenyl ether, and POE dinonylphenyl ether; pluronic-type substances such as pluronic; POE/POP alkyl ethers such as POE/POP cetyl other, POE/POP monobutyl ether, POE/POP 2-decyltetradecyl ether, POE/POP monobutyl ether, and POE/POP hydrogenated lanolin; tetra POE/tetra POP ethylenediamine condensate such as tetronic; POE castor oil derivatives such as POE castor oil, POE hydrogenated castor oil, POE hydrogenated castor oil monoisostearate, POE hydrogenated castor oil triisostearate, POE hydrogenated castor oil monopyroglutamate diester, and POE hydrogenated castor oil maleate; POE beeswax or POE lanolin derivatives such as POE sorbitol beeswax; alkanol amides such as coconut fatty acid diethanolamide, lauric acid monoethanolamide, and fatty acid isopropanolamide; POE fatty acid amides; sucrose fatty acid esters; POE nonylphenyl formaldehyde condensates; alkylethoxydimethylamine oxides; and trioleyl phosphate.

Examples of anionic surfactants include fatty acid soaps such as bases for soaps, sodium laurate, sodium palmitate, and sodium stearate; higher alkyl sulfate such as sodium lauryl sulfate and potassium lauryl sulfate; alkyl ether sulfate such as triethanolamine POE lauryl sulfate and sodium POE lauryl sulfate; N-acyl sarcosine such as sodium lauroyl sarcosinate; higher fatty acid amide sulfonate such as sodium N-myristoyl-N-methyl taurate, sodium N-cocoyl-N-methyl tauride, and sodium lauryl methyl tauride; phosphate such as sodium POE oleyl ether phosphate and POE stearyl ether phosphate; sulfosuccinates such as sodium di-2-ethylhexyl sulfosuccinate and sodium monolauroyl monoethanolamide polyoxyethylenesulfosuccinate; alkyl benzene sulfonates such as linear sodium dodecylbenzenesulfonate, linear triethanolamine dodecylbenzenesulfonate, and linear dodecylbenzenesulfonic acid; N-acyl glutamates such as monosodium N-lauroyl glutamate, disodium N-stearoyl glutamate, and monosodium N-myristoyl-L-glutamate; higher fatty acid ester sulfates such as sodium hydrogenated castor oil fatty acid glyceride sulfate; sulfated oils such as Turkey red oil; POE alkyl ether carboxylic acids; POE alkyl ether carboxylates; α-olefin sulfonates; higher fatty acid alkylolamide sulfonate; sodium lauroyl monoethanolamide succinate; di-triethanolamine N-palmitoyl aspartate; and sodium caseinate.

Examples of cationic surfactants include alkyl trimethyl ammonium salts such as stearyl trimethyl ammonium chloride and lauryl trimethyl ammonium chloride; dialkyl dimethyl ammonium salts such as distearyl dimethyl ammoniumchloride; alkyl pyridinium salts such as poly(N,N-dimethyl-3,5-methylene piperidinium) chloride and cetyl piperidinium chloride; alkyl quaternary ammonium salts; alkyl dimethyl benzyl ammonium salts; alkyl isoquinolium salts; dialkyl monophonium salts; POE alkylamines; alkylamine salts; polyamine fatty acid derivatives; amylalcohol fatty acid derivatives; benzalkonium chloride; and benzethonium chloride.

Examples of ampholytic surfactants include imidazoline type ampholytic surfactants such as sodium 2-undecyl-N,N,N-(hydroxyethylcarboxylmethyl)- 2-imidazoline and disodium 2-cocoyl-2-imidazolinium-1-carboxyethyloxy hydroxide; and betaine type ampholytic surfactants such as 2-heptadecyl-N-carboxymethyl-N-hydroxyethylimidazolinium betaine, lauryl dimethylaminoacetic acid betaine, alkyl betaine, amide betaine, and sulfobetaine.

These surfactants may be used alone as well as in combination of two or more. Though the compounding amount thereof is not restricted in particular, 0.01 to 20 weight % thereof is preferably compounded in the whole composition when an emulsion is to be obtained. A stable emulsion may not be obtained when the compounding amount is less than 0.01 weight %, whereas the feel of use may deteriorate when the amount exceeds 20 weight %.

As the aqueous medium, water may be used alone or in combination with ethanol, glycerin, polyethylene glycol, propylene glycol, dipropylene glycol, 1,3-butanediol, xylitol, sorbitol, maltitol, chondroitin sulfate, hyaluronic acid, mucoitin sulfate, caronic acid, atherocollagen, cholesteryl-12-hydroxy stearate, sodium lactate, bile salt, dl-pyrrolidone carboxylate, short-chain soluble collagen, diglycerin (EO) PO addition products, Rosa roxburghii extract, yarrow extract, sweet clover extract, or the like. Though the compounding amount of these aqueous media is not restricted in particular, preferably 0.1 to 40 weight % and more preferably 2 to 30 weight % thereof is compounded in the whole composition when an emulsion is to be obtained. Feel of the composition may become worse when the amount is less than 0.1 weight %, whereas a stable emulsion may not be obtained when the amount exceeds 40 weight %.

Examples of oily ingredients are as follows. Among them, examples of liquid oils include avocado oil, tsubaki oil, turtle oil, macadamia nut oil, corn oil, mink oil, olive oil, rape seed oil, egg yolk oil, sesame oil, persic oil, wheat germ oil, sasanqua oil, castor oil, linseed oil, safflower oil, cottonseed oil, perilla oil, soybean oil, peanut oil, tea seed oil, kaya oil, rice bran oil, China tung oil, Japanese tung oil, jojoba oil, germ oil, triglycerol, glyceryl trioctanoate, pentaerythritol tetraoctanoate, and glyceryl tiisopalmitate.

Examples of solid fats include cacao fat, coconut oil, hydrogenated coconut oil, palm oil, palm kernel oil, Japan wax kernel oil, hydrogenated oils, Japan wax, and hydrogenated castor oil.

Examples of waxes include beeswax, candelilla wax, cotton wax, carnauba wax, bayberry wax, Chinese wax, spermaceti, montan wax, bran wax, lanolin, kapok wax, lanolin acetate, liquid lanolin, cane wax, isopropanol lanolin fatty acid ester, hexyl laurate, hydrogenated lanolin, jojoba wax, hard lanolin, shellac wax, POE lanolin alcohol ether, POE lanolin alcohol acetate, POE cholesterol ether, polyethylene glycol lanolin fatty acid ester, and POE hydrogenated lanolin alcohol ether.

Examples of hydrocarbon oils include liquid paraffin, ozokenrte, squalene, pristane, paraffin, ceresin, squalane, vaseline, and microcrystalline wax.

Examples of synthetic ester oils include isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexanoate, dipentaerythritol fatty acid ester, N-alkyl glycol monoisostearate, neopentyl glycol dicaprate, diisostearyl malate, glyceryl di-2-heptylundecanoate, trimethylolpropane tri-2-ethylhexanoate, trimethylolpropane triisostearate, pentaerythritol tetra-2-ethylhexanoate, glyceryl tri-2-ethylhexanoate, trimethylolpropane triisostearate, cetyl 2-ethylhexanoate, 2-ethylhexyl palmitate, glyceryl trimyristate, tri-2-heptylundecanic acid glyceride, castor oil fatty acid methyl ester, oleyl oleate, acetoglyceride, 2-heptylundecyl palmitate, N-lauroyl-L-glutamate-2-octyldodecyl ester, ethyl laurate, di-2-ethylhexyl sebacate, 2-hexyldecyl myristate, 2-hexyldecyl palmitate, mono-2-hexyldecyl adipate, diisopropyl sebacate, mono-2-ethylhexyl succinate, ethyl acetate, butyl acetate, amyl acetate, and triethyl citrate.

Examples of silicones include chain polysiloxanes such as dimethyl polysiloxane, methyl phenyl polysiloxane, and methyl hydrogen polysiloxane; and cyclic silicones such as octamethylcyclotetrasiloxane, decamethylcyclopentasiloxane, and dodecamethylcyclohexasiloxane.

Though the compounding amount of these oily ingredients is not restricted in particular, preferably 0.5 to 60 weight % and more preferably 2.5 to 45 weight % thereof is compounded in the whole composition when an emulsion is to be obtained.

Examples of higher alcohols include straight-chain alcohols such as lauryl alcohol, cetyl alcohol, stearyl alcohol, behenyl alcohol, myristyl alcohol, oleyl alcohol, and cetostearyl alcohol; and branched alcohols such as monostearyl glycerin ether (batyl alcohol), 2-decyltetradecinol, lanolin alcohol, cholesterol, phytosterol, hexyldodecanol, isostearyl alcohol, and octyldodecanol.

Examples of metal-ion blocking agents include 1-hydroxyethane-1,1-diphosphonic acid, tetrasodium 1-hydroxyethane-1,1-diphosphonate, disodium edetate, trisodium edetate, tetrasodium edetate, sodium citrate, sodium polyphosphate, sodium metaphosphate, gluconic acid, phosphoric acid, citric acid, ascorbic acid, citric acid, and edetic acid.

Examples of natural water-soluble polymers include vegetable polymers such as gum arabic, tragacanth gum, galactan, guar gum, carob gum, karaya gum, carrageenan, pectin, agar, quince seed, algae-colloid (brown algae extract), starch (rice, corn, potato, and wheat), and glycyrrhizinic acid; microbiological polymers such as xanthan gum, dextran, succinoglucan, and pullulan; and animal polymers such as collagen, casein, albumin, and gelatin.

Examples of semi-synthetic water-soluble polymers include starch polymers such as carboxymethyl starch and methylhydroxypropyl starch; cellulose polymers such as methylcellulose, nitrocellulose, ethylcellulose, methylhydroxypropylcellulose, hydroxyethylcellulose, sodium cellulose sulfate, hydroxypropylcellulose, sodium carboxymethylcellulose (CMC), crystalline cellulose, and cellulose powder; and alginate polymers such as sodium alginate and propylene glycol alginate.

Examples of synthetic water-soluble polymers include vinyl polymers such as polyvinyl alcohol, polyvinyl methyl ether, polyvinyl pyrrolidone, and carboxyvinyl polymer (Carbopol); polyoxyethylene polymers such as polyethylene glycol 20,000, 6,000, and 4,000; copolymers such as polyoxyethylene/polyoxypropylene copolymer; acrylic polymers such as sodium polyacrylate, polyethyl acrylate, and polyacrylamide; polyethyleneimine; and cation polymers.

Examples of inorganic water-soluble polymers include bentonite, aluminum magnesium silicate (Veegum), laponite, hectorite, and silicic anhydride.

Examples of ultraviolet absorbers include benzoic acid ultraviolet absorbers such as p-aminobenzoic acid (referred to as "PABA" hereinafter), PABA monoglycerin ester, N,N-dipropoxy PABA ethyl ester, N,N-diethoxy PABA ethyl ester, N,N-dimethyl PABA ethyl ester, and N,N-dimethyl PABA butyl ester; anthoranilic acid ultraviolet absorbers such as homomethyl-N-acetyl anthoranilate; salicylic acid ultraviolet absorbers such as amyl salicylate, menthyl salicylate, homomenthyl salicylate, octyl salicylate, phenyl salicylate, benzyl salicylate, and p-isopropanol phenyl salicylate; cinnamic acid ultraviolet absorbers such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, octyl-p-methoxy cinnamate (2-ethylhexyl-p-methoxy cinnamate), 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate, and glyceryl mono-2-ethyl-hexanoyl-diparamethoxy cinnamate; benzophenone ultraviolet absorbers such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenylbenzophenone-2-carboxylate, 2-hydroxy-4-n-octoxybenzophenone, and 4-hydroxy-3-carboxybenzophenone; 3-(4'-methylbenzylidene)-d,1-camphor; 3-benzylidene-d,1-camphor; urocanic acid; ethyl urocanate; 2-phenyl-5-methylbenzoxazol; 2,2'-hydroxy-5-methylphenyl benzotriazol; 2-(2'-hydroxy-5'-t-octylphenyl) benzotriazol; 2-(2'-hydroxy-5'-methylphenyl)benzotriazol; dibenzaladine; dianisoyl methane; and 5-(3,3'-dimethyl-2-norbornylidene)-3-pentane-2-on.

Examples of blood circulation-accelerating agents include such drugs as nonylic acid valerylamide, benzyl nicotinate, β-butoxyethyl nicotinate, capsaicin, zingerone, cantharides tincture, ichthammol, caffeine, tannic acid, α-borneol, tocopherol nicotinate, inositol hexanicotinate, cyclandelate, cinnatizine, tolazoline, acetylcholine, verapamil, cepharanthine, and γ-oryzanol. These drugs may be used not only in their free states but also in the form of salts of acid or base when they can form such salts or in the form of esters when they can be esterified.

In the following, the present invention will be explained in further detail with reference to examples in which diisopropyl adipate or dioctyl succinate are respectively used as the diester of the essential ingredient (B) in the present invention. In the following, compounding amounts will be expressed in terms of weight % with respect to the composition unless otherwise specified.

Experiment 1

Stability over Time and Feel of Use

First, milky lotions were prepared in accordance with prescriptions shown in Table 1 below. The method of preparation comprises the steps of heating the respective groups of ingredients for oil phase and water phase to 70° C. so as to be completely dissolved, mixing the oil phase into the water phase, and then emulsifying the mixture by means of an emulsifier. The resulting emulsion was cooled to a final temperature of 30° C. by means of a heat exchanger, whereby W/O-type ultraviolet absorbing milky lotions were obtained.

For each milky lotion, stability over time and feel of use were evaluated according to the following methods.

(Stability over Time)

Each milky lotion was put into a container and stored for one month at −5° C. and 0° C. Thereafter, microscopic observation was performed. Standard for evaluation was as follows:

Standard for Evaluating Stability over Time

○: No crystals of 4-tert-butyl-4'-methoxydibenzoylmethane are observed.

Δ: Crystals of 4-tert-butyl-4'-methoxydibenzoylmethane are slightly observed.

X: Crystals of 4-tert-butyl-4'-methoxydibenzoylmethane are considerably observed.

(Feel of Use)

Each milky lotion was continuously applied to faces and upper arms of 10 female panels once a day for 3 weeks. Then, the panels were asked about the feel of use of the lotion by means of a questionnaire. The results were evaluated according to the following standards for evaluation:

Standard for Evaluating Feel of Use

○: Not more than 2 panels evaluated the sample as sticky.

Δ: At least 3 but not more than 6 panels evaluated the sample as sticky.

X: 7 or more panels evaluated the sample as sticky.

TABLE 1

| | Sample No. | | | | |
|---|---|---|---|---|---|
| Ingredient | 1-1 | 1-2 | 1-3 | 1-4 | 1-5 |
| Oil phase: | | | | | |
| Diisopropyl adipate | 15.0 | — | — | — | — |
| Dioctyl succinate | — | 15.0 | — | — | — |
| Glyceryl tri-2-ethyl-hexanoate | — | — | — | — | 15.0 |
| Pentaerythritol tetra-2-ethylhexanoate | — | — | 15.0 | 10.0 | — |
| 4-tert-butyl-4'-methoxydibenzoyl-methane | 5.0 | 5.0 | 5.0 | 5.0 | 5.0 |
| Stearyl alchol | 3.0 | 3.0 | 3.0 | 3.0 | 3.0 |
| Octyl methoxycinnamate | 5.0 | 5.0 | 5.0 | 5.0 | 5.0 |
| Stearic acid | 0.5 | 0.5 | 0.5 | 0.5 | 0.5 |
| Behenic acid | 0.5 | 0.5 | 0.5 | 0.5 | 0.5 |
| Glyceryl monostearate, selfemulsifying | 1.0 | 1.0 | 1.0 | 1.0 | 1.0 |
| POE (5) glyceryl monostearate | 1.0 | 1.0 | 1.0 | 1.0 | 1.0 |
| Water phase: | | | | | |
| Carboxyvinyl polymer | 0.2 | 0.2 | 0.2 | 0.2 | 0.2 |
| Triethanolamine | 0.4 | 0.4 | 0.4 | 0.4 | 0.4 |
| Propylene glycol | 10.0 | 10.0 | 10.0 | 10.0 | 10.0 |
| Ethanol | 5.0 | 5.0 | 5.0 | 5.0 | 5.0 |
| Methyl p-oxybenzoate | 0.1 | 0.1 | 0.1 | 0.1 | 0.1 |
| Trisodium edetate | 0.1 | 0.1 | 0.1 | 0.1 | 0.1 |
| Ion-exchanged water | balance | balance | balance | balance | balance |
| Total | 100 | 100 | 100 | 100 | 100 |
| Stability of Storage at −5° C. | 0 | 0 | Δ | x | Δ |
| Stability of Storage at 0° C. | 0 | 0 | Δ | x | Δ |
| Feel of Use | 0 | 0 | x | Δ | Δ |

As can be seen from Table 1, in the lotions of Sample 1-3 to 1-5 using a polyhydric alcohol fatty acid ester (glyceryl tri-2-ethylhexanoate or pentaerythritol tetra-2-ethylhexanoate), which has conventionally been used for stably compounding 4-tert-butyl-4'-methoxydibenzoylmethane of (A), though (A) had been uniformly dissolved immediately after the manufacture thereof, deposition of crystals of (A) was observed after the storage for one month at −5° C. and at 0° C. When (A) is deposited as a crystal, the ultraviolet absorbing effect of the composition containing it remarkably deteriorates. Also, the lotions of Sample 1-3 to 1-5 exhibited stickiness, thereby yielding unfavorable feel of use.

By contrast, in the lotions of Sample 1—1 and 1-2 in accordance with the present invention using a diester (diisopropyl adipate or dioctyl succinate), no deposition of crystal of (A) was observed even after the storage for one month at −5° C. and at 0° C., whereby these lotions could stably exhibit the aimed ultraviolet absorbing effect. Also, since the diester is used, these milky lotions exhibited refreshing feel of use which was free of stickiness and a high concentration of (A) could be compounded therein. Also, irritation such as stingingness or itch did not occur.

In view of the foregoing, it can be understood that the ultraviolet absorbing composition of the present invention exhibits a favorable stability over time and excellent feel of use and safety even when a high concentration of 4-tert-butyl-4'-methoxydibenzoylmethane is compounded therein.

Experiment 2

Compounding Amount of Diester

Next, in the prescription of Sample 1—1 or 1-2 mentioned above, while the compounding amount of diester (B) was changed as shown in Tables 2 and 3, milky lotions were similarly prepared, whereby the influence of the compounding amount of (B) upon the stability over time was studied. Here, the compounding amount of (A), 4-tert-butyl-4'-methoxydibenzoylmethane, was fixed to 6.0 weight % in the composition, while changes in amounts of (A) and (B) were adjusted by ion-exchanged water.

TABLE 2

| | Sample No. | | | |
|---|---|---|---|---|
| Ingredient | 2-1 | 2-2 | 2-3 | 2-4 |
| Diisopropyl adipate | 1.0 | 2.0 | 10.0 | 30.0 |
| 4-tert-butyl-4'-methoxydibenzoylmethane | 6.0 | 6.0 | 6.0 | 6.0 |
| Stability of Storage at −5° C. | x | 0 | 0 | 0 |
| Stability of Storage at 0° C. | Δ | 0 | 0 | 0 |

TABLE 3

| | Sample No. | | | |
|---|---|---|---|---|
| Ingredient | 2-5 | 2-6 | 2-7 | 2-8 |
| Dioctyl succinate | 1.0 | 2.0 | 10.0 | 30.0 |
| 4-tert-butyl-4'-methoxydibenzoylmethane | 6.0 | 6.0 | 6.0 | 6.0 |
| Stability of Storage at −5° C. | x | 0 | 0 | 0 |
| Stability of Storage at 0° C. | Δ | 0 | 0 | 0 |

As can be seen from Tables 2 and 3, when the compounding amount of diester was smaller than one third of that of (A) in terms of weight, deposition of crystal of (A) might be observed after the storage for one month at −5° C. and 0° C.

By contrast, when the compounding amount of diester was not smaller than one third of that of (A), no crystals were deposited after the storage for one month at −5° C. and 0° C., thereby exhibiting a favorable stability over time. Also, even when diester was compounded in excess, no problem was observed in terms of stability over time, feel of use, and safety.

In view of the foregoing, in the ultraviolet absorbing composition in accordance with the present invention, the compounding amount of diester of (B) in the composition with respect to 4-tert-butyl-4'-methoxydibenzoylmethane of (A) in the composition is preferably at least one third in terms of weight.

Experiment 3

Compoundings Amount in The Oil Phase

Next, while the oil phase shown in Table 4 below was used in spite of the oil phase of Sample 1—1 mentioned above, milky lotions were similarly prepared, whereby the stability over time and feel of use were studied.

TABLE 4

| Ingredient | 3-1 | 3-2 | 3-3 | 3-4 | 3-5 |
|---|---|---|---|---|---|
| Oil phase: | | | | | |
| Dioctyl succinate | — | — | — | 2.0 | 5.0 |
| Pentaerythritol tetra-2-ethylhexanoate | 2.0 | 5.0 | 2.0 | — | — |
| 4-tert-butyl-4'-methoxydibenzoyl-methane | 0.8 | 1.0 | 0.5 | 0.8 | 1.0 |
| Stearyl alchol | 3.0 | 3.0 | 3.0 | 3.0 | 3.0 |
| Octyl methoxycinnamate | 5.0 | 5.0 | 5.0 | 5.0 | 5.0 |
| Stearic acid | 0.5 | 0.5 | 0.5 | 0.5 | 0.5 |
| Behenic acid | 0.5 | 0.5 | 0.5 | 0.5 | 0.5 |
| Glyceryl monostearate, selfemulsifying | 1.0 | 1.0 | 1.0 | 1.0 | 1.0 |
| POE (5) glyceryl monostearate | 1.0 | 1.0 | 1.0 | 1.0 | 1.0 |
| Water phase (as same as TABLE 1): | balance | balance | balance | balance | balance |
| Total | 100 | 100 | 100 | 100 | 100 |
| (A)/(Oil phase) × 100 (%) | 5.8 | 5.9 | 3.7 | 5.8 | 5.9 |
| Stability of Storage at −5° C. | Δ | 0 | 0 | 0 | 0 |
| Stability of Storage at 0° C. | Δ | 0 | 0 | 0 | 0 |
| Feel of Use | 0 | Δ | 0 | 0 | 0 |

As can be seen from Table 4, when a conventionally used oil(pentaerythritol tetra-2-ethylhexanoate) is used, in cases where the concentration of (A) in the oil phase becomes 5 weight % or greater, it is impossible to yield a composition in which deposit of crystals of (A) and stickiness are prevented from occurring (Sample 3-1 to 3—3).

By contrast, when diester of (B) in accordance with the present invention (dioctyl succinate) is used, even in cases where the concentration of (A) in the oil phase is 5 weight % or greater, crystals are prevented from depositing without generating stickiness.

Accordingly, in accordance with the present invention, crystals of (A) are prevented depositing without generating stickiness not only when (A) is at a low concentration in the oil phase but also when (A) is at a high concentration. The present invention is useful in particular when, for example, the concentration of (A) in the oil phase is 5 weight % or greater.

Example 1
W/O Ultraviolet Absorbing Milky Lotion
(Prescription)

| | |
|---|---|
| Oil phase: | |
| Palmitic acid | 0.1 |
| Behenic acid | 0.1 |
| Dihexyl succinate | 6.0 |
| Octyl palmitate | 5.0 |
| Glyceryl tri-2-ethylhexanoate | 5.0 |
| Cetyl alcohol | 1.0 |
| Stearyl alcohol | 1.0 |
| Decamethylcylopentasiloxane | 20.0 |
| Glyceryl di-para-methoxycinnamate mono-2-ethylhexanoate | 3.0 |
| 4-tert-butyl-4'-methoxydibenzoylmethane | 2.0 |
| Polyoxyethylene/methylpolysiloxane copolymer | 2.0 |
| Sorbitan monostearate | 0.5 |
| Globular polyethylene (10 μ) | 0.2 |

-continued

Example 1
W/O Ultraviolet Absorbing Milky Lotion
(Prescription)

| | |
|---|---|
| Perfume | 0.1 |
| Water Phase: | |
| Ethanol | 5.0 |
| Paraben | 0.2 |
| Rosa roxburghii extract | 0.2 |
| Sodium 2-hydroxy-4-methoxybenzophenone-5-sulfonate | 0.1 |
| Fennel extract | 0.1 |
| Dipropylene glycol | 2.0 |
| Pottasium hydroxide | 0.2 |
| Ion-exchanged water | to 100 |

(Preparation Method)

The respective groups of ingredients for oil phase (except for globular polyethylene) and water phase was heated to 70° C. so as to be dissolved. Globular polyethylene was sufficiently suspended in the oil phase and the water phase was added into the resulting suspension while emulsifying by means of a homogenizer. The resulting emulsion was cooled by means of a heat exchanger, whereby a W/O-type ultraviolet absorbing milky lotion was obtained.

Example 2
O/W Ultraviolet Absorbing Sunscreen Cream
(Prescription)

| | |
|---|---|
| Oil phase: | |
| Octyl methoxycinnamate | 8.0 |
| 4-tert-butyl-4'-methoxydibenzoylmethane | 8.0 |
| Pentaerythritol tetra-2-ethylhexanoate | 3.0 |
| 2-hydroxy-4-methoxybenzophenone | 3.0 |
| Dioctyl succinate | 24.0 |
| Particulate titanium dioxide | 7.0 |
| Squalane | 20.0 |
| Polyoxyethylene/methylpolysiloxane copolymer | 3.0 |
| Organophilic montmorillonite | 1.5 |
| Silicone powder (5 μ) | 5.0 |
| Paraben | 0.2 |
| Perfume | 0.1 |
| γ-oryzanol | 0.1 |
| Water phase: | |
| Glycerin | 3.0 |
| Placenta extracts | 0.1 |
| Trisodium edetate | 0.2 |
| Ion-exchanged water | to 100 |

(Preparation Method)

The water phase was heated to 70° C. so as to be dissolved. The oil phase except for titanium dioxide and silicone powder were heated to dissolved and then titanium dioxide and silicone powder was sufficiently suspended therein. The oil phase was added into the water phase while emulsifying by means of a homogenizer and the resulting emulsion was cooled by means of a heat exchanger, whereby an O/W-type ultraviolet absorbing sunscreen cream was obtained.

Example 3
O/W Ultraviolet Absorbing Cream
(Prescription)

| | |
|---|---|
| Oil phase: | |
| Glyceryl di-para-methoxycinnamate | 1.0 |

-continued

Example 3
O/W Ultraviolet Absorbing Cream
(Prescription)

| | |
|---|---|
| mono-2-ethylhexanoate | |
| 4-tert-butyl-4'-methoxydibenzoylmethane | 1.0 |
| 2-hydroxy-4-methoxybenzophenone | 1.0 |
| Cetyl alcohol | 1.0 |
| Diisopropyl adipate | 3.0 |
| Particulate titanium dioxide | 0.5 |
| Squalane | 20.0 |
| Vaseline | 1.0 |
| Jojoba oil | 1.0 |
| Glyceryl monostearate | 3.0 |
| Organophilic montmorillonite | 1.5 |
| Polymethylmethacrylate (particle size is 8 μ) | 2.0 |
| Paraben | 0.2 |
| Perfume | 0.1 |
| Water phase: | |
| Glycerin | 3.0 |
| Sweet clover extract | 0.5 |
| Ion-exchanged water | to 100 |

(Preparation Method)

In the same manner to Example 2, an O/W-type ultraviolet absorbing cream was obtained.

Example 4
O/W Ultraviolet Absorbing Cream
(Prescription)

| | |
|---|---|
| Oil phase: | |
| Stearic acid | 4.0 |
| Stearyl alcohol | 4.0 |
| Glyceryl monostearate | 3.0 |
| Vitamin E acetate | 0.05 |
| Perfume | 0.1 |
| Ethyl paraben | 0.1 |
| Butyl paraben | 0.1 |
| Diethyl malonate | 5.0 |
| Octyl methoxycinnamate | 1.0 |
| 4-tert-butyl-4'-methoxydibenzoylmethane | 1.0 |
| Water phase: | |
| 1,3-butylene glycol | 3.0 |
| Propylene glycol | 3.0 |
| Glycerin | 2.0 |
| Pottasium hydroxide | 0.4 |
| Ion-exchanged water | to 100 |

(Preparation Method)

The water phase was heated to 70° C. and the oil phase heated to dissolved was added into therein while emulsifying by means of a homogenizer. The resulting emulsion was cooled by means of a heat exchanger, whereby an O/W-type ultraviolet absorbing cream was obtained.

Example 5
Q/W Ultraviolet Absorbing Milky Lotion
(Prescription)

| | |
|---|---|
| Oil phase: | |
| Squalane | 5.0 |
| Oleyl oleate | 3.0 |
| Methyl phenyl polysiloxane | 1.0 |
| Vaseline | 1.0 |
| Sorbitan sesquioleate | 0.8 |
| Polyoxyethylene (20) oleyl ether | 1.2 |
| Octyl methoxycinnamate | 3.0 |
| 4-tert-butyl-4'-methoxydibenzoylmethane | 5.0 |

-continued

Example 5
Q/W Ultraviolet Absorbing Milky Lotion
(Prescription)

| | |
|---|---|
| 2-hydroxy-4-methoxybenzophenone | 2.0 |
| Dibutyl malonate | 15.0 |
| Perfume | 0.3 |
| Water phase: | |
| Dipropylene glycol | 3.0 |
| ethanol | 5.0 |
| Carboxyvinylpolymer | 0.2 |
| Sodium hyaluronate | 0.01 |
| Pottasium hydroxide | 0.08 |
| Methyl paraben | 0.15 |
| Sodium hexamataphosphate (extra pure grade reagent) | 0.02 |
| Trisodium edetate | 0.05 |
| Ion-exchanged water | to 100 |

(Preparation Method)

In the same manner to Example 4, an O/W-type ultraviolet absorbing milky lotion was obtained.

Example 6
O/W Ultraviolet Absorbing Essence
(Prescription)

| | |
|---|---|
| Oil phase: | |
| Stearic acid | 1.0 |
| Cetyl alcohol | 1.3 |
| Lanolin derivative | 2.0 |
| Liquid paraffin | 2.0 |
| Dihexyl succinate | 5.0 |
| POE cetyl ether | 1.0 |
| Glyceryl monostearate | 2.0 |
| Glyceryl di-para methoxycinnamate mono-2-ethylhexanoate | 0.5 |
| 4-tert-butyl-4'-methoxydibenzoylmethane | 1.5 |
| Butyl paraben | appropriate amount |
| Ethyl paraben | appropriate amount |
| Water phase: | |
| 1,3-butylene glycol | 6.0 |
| Sodium 2-hydroxy-4-methoxybenzophenone-5-sulfonate | 0.05 |
| Triethanolamine | 3.0 |
| Placenta extract | 0.01 |
| Rosa roxburghii extract | 0.1 |
| Ion-exchanged water | to 100 |

(Preparation Method)

In the same manner to Example 4, an O/W-type ultraviolet absorbing essence was obtained.

Example 7
W/O Ultraviolet Absorbing Sunscreen Cream
(Prescription)

| | |
|---|---|
| Oil phase: | |
| Dioctyl succinate | 40.0 |
| Octyl methoxycinnamate | 7.0 |
| 4-tert-butyl-4'-methoxydibenzoylmethane | 5.0 |
| Decamethylcyclopentasiloxane | 10.0 |
| 2-hydroxy-4-methoxybenzophenone | 2.0 |
| Particulate zinc oxide treated to be hydrophobic | 5.0 |
| Titanium dioxide treated to be hydrophobic | 4.0 |
| Organophilic montmorillonite | 2.0 |
| Antiseptic agent | 0.3 |
| Perfume | 0.2 |
| Water phase: | |
| 1,3-butylene glycol | 6.0 |

Example 7
W/O Ultraviolet Absorbing Sunscreen Cream
(Prescription)

| | |
|---|---|
| Trisodium edetate | 0.2 |
| Ion-exchanged water | to 100 |

(Preparation Method)

The oil phase except for titanium dioxide treated to be hydrophobic and particulate zinc oxide treated to be hydrophobic was heated at 70° C. to dissolved and then those powders were sufficiently suspended therein. The water phase was added into the oil phase while emulsifying by means of a homogenizer and the resulting emulsion was cooled by means of a heat exchanger, whereby a W/O-type ultraviolet absorbing sunscreen cream was obtained.

Example 8
W/O Ultraviolet Absorbing Cream
(Prescription)

| | |
|---|---|
| Oil phase: | |
| Glyceryl di-para-methoxycinnamate mono-2-ethylhexanoate | 1.0 |
| 4-tert-butyl-4'-methoxydibenzoylmethane | 1.0 |
| 2-hydroxy-4-methoxybenzophenone | 1.0 |
| Cetyl alcohol | 1.0 |
| Particulate titanium dioxide | 0.5 |
| Squalane | 20.0 |
| Vaseline | 1.0 |
| Diisopropyl adipate | 30.0 |
| Jojoba Oil | 1.0 |
| Glyceryl monostearate | 3.0 |
| Aluminum magnesium silicate | 2.0 |
| Distearyl dimethyl ammonium chloride | 1.0 |
| Paraben | 0.2 |
| Perfume | 0.1 |
| Water phase: | |
| Glycerin | 3.0 |
| Sweet clover extract | 0.5 |
| Ion-exchanged water | to 100 |

(Preparation Method)

In the same manner to Example 7, a W/O-type ultraviolet absorbing cream was obtained.

Any of Examples 1 to 8 is an ultraviolet absorbing compositions which has a favorable stability over time, is excellent in feel of use and safety, and exhibits a favorable ultraviolet absorbing effect.

As explained foregoing, in accordance with the present invention, by using a specific diester, even when a high concentration of 4-tert-butyl-4'-methoxydibenzoylmethane which is hardly soluble UV-A absorber is compounded therein, it is able to obtain an ultraviolet absorbing composition which exhibits a favorable stability over time, is free from oily feel and sticky feel, yields a refreshing feel of use, and exhibits a high safety.

What is claimed is:

1. An ultraviolet absorbing composition comprising:
   (A) 4-tert-butyl-4'-methoxydibenzoylmethane; and
   (B) a diester which is dioctyl succinate; and
   (C) an oil phase, wherein said oil phase contains at least one selected from the group consisting of liquid oil, wax, hydrocarbon oil, synthetic ester oil, silicone, and higher alcohol,
   wherein (A) and (B) are dissolved in said oil phase and the amount of (B) in the whole composition is at least one third of the amount of (A) in the whole composition by weight.

2. An ultraviolet absorbing composition according to claim 1, wherein (A) has a concentration of at least 5 weight % in said oil phase.

3. An ultraviolet absorbing composition according to claim 1, consisting of:
   (A) 4-tert-butyl-4'-methoxydibenzoylmethane;
   (B) a diester which is dioctyl succinate;
   (C) an oil phase, wherein said oil phase contains at least one selected from the group consisting of liquid oil, wax, hydrocarbon oil, synthetic ester oil, silicone, and higher alcohol,
   wherein (A) and (B) are dissolved in said oil phase and the amount of (B) in the whole composition is at least one third of the amount of (A) in the whole composition by weight; and
   (D) a water phase, wherein said water phase contains at least water.

4. An ultraviolet absorbing composition according to claim 1, consisting of:
   (A) 4-tert-butyl-4'-methoxydibenzoylmethane;
   (B) a diester which is dioctyl succinate;
   (C) an oil phase, wherein said oil phase contains at least one selected from the group consisting of liquid oil, wax, hydrocarbon oil, synthetic ester oil, silicone, and higher alcohol,
   wherein (A) and (B) are dissolved in said oil phase and the amount of (B) in the whole composition is at least one third of the amount of (A) in the whole composition by weight;
   (D) a water phase, wherein said water phase contains at least water; and
   (E) a solid phase, wherein said solid phase contains at least one of inorganic and organic powder.

5. A method for protecting human skin or hair from ultraviolet rays comprising:
   applying said ultraviolet absorbing composition according to claim 1 on human skin or hair.

* * * * *